United States Patent [19]

Frenkel et al.

[11] Patent Number: 6,007,569
[45] Date of Patent: Dec. 28, 1999

[54] QUANTIFYING STRESS REDUCTION AND MEDICAL TREATMENT AS A RESULT OF COLORED LIGHT THERAPIES

[76] Inventors: Richard E. Frenkel; Barbara G. Frenkel, both of 14 Wyndham Close, White Plains, N.Y. 10605

[21] Appl. No.: 09/195,586

[22] Filed: Nov. 18, 1998

Related U.S. Application Data

[63] Continuation-in-part of application No. 08/801,887, Feb. 18, 1997, abandoned.

[51] Int. Cl.[6] .................................................... A61N 5/01
[52] U.S. Cl. ................................ 607/88; 600/26; 600/27; 600/545
[58] Field of Search ................................ 607/88, 90, 91, 607/94; 600/26, 27, 544, 545, 300, 485, 524; 128/905

[56] References Cited

U.S. PATENT DOCUMENTS

| | | |
|---|---|---|
| 4,327,712 | 5/1982 | Frenkel et al. . |
| 5,064,410 | 11/1991 | Frenkel et al. . |
| 5,562,707 | 10/1996 | Prochazka et al. .......................... 607/2 |
| 5,792,047 | 8/1998 | Coggins .................................... 600/300 |

Primary Examiner—Linda C. M. Dvorak
Assistant Examiner—Rosiland Kearney
Attorney, Agent, or Firm—Salzman & Levy

[57] ABSTRACT

The present invention features an apparatus for quantifying the effects that colored light therapies and treatments have upon an individual. The apparatus features an imagescope console that bathes a patient in different light colors, patterns, sequences, hues, tints, etc. A physiological monitoring unit monitors the bodily functions of the individual as the various colored light treatments are applied. A computer analyzes the monitored data, and produces a printout, or an electrostressogram, which details the quantitative effects of the light therapies. The electrostressogram can be faxed or otherwise transmitted to medical offices, and/or satellite communicated from spacecrafts and interplanetary space station to Earth for screening, preventing, diagnosing, and treating medical illnesses caused by stress.

20 Claims, 2 Drawing Sheets

US 6,007,569

QUANTIFYING STRESS REDUCTION AND MEDICAL TREATMENT AS A RESULT OF COLORED LIGHT THERAPIES

This application is a continuation-in-part of application Ser. No. 08/801,887 filed on Feb. 18, 1997, now abandoned.

FIELD OF THE INVENTION

The present invention pertains to the prevention and treatment of stress through the use of colored light therapy and, more particularly, to a computerized system for physiologically measuring the effects that different colored light therapies have upon an individual in the treatment of stress and other related conditions, disorders and diseases.

DESCRIPTION OF RELATED ART

In U.S. Pat. No. 4,327,712 (issued to FRENKEL et al on May 4, 1982), a device called an "imagescope" is described. This imagescope bathes the face of a viewer in different colors of light, and determines for a given individual which colors are stressful and which calmative.

In U.S. Pat. No. 5,064,410 (issued to FRENKEL et al on Nov. 12, 1991), a pair of colored eyeglasses is used, in conjunction with the imagescope of the aforementioned patent, to relieve an individual's stress during one's daily, stress-filled activities

BACKGROUND OF THE INVENTION

It has been known for many years that individuals are physically and psychologically affected by different light frequencies, colors, strobe lights, flashing lights, light intensities, daily light duration and light deprivation. Recently, members of both the medical and pharmaceutical research realms have been conducting experiments and developing new light therapies in conjunction with drugs in the treatment of disease. For example, in the treatment of tumors, light is being used to activate substances that cause necrosis of the tumorous tissue. Light is also being used to activate drugs that are therapeutic, as well as to eliminate side effects of certain drug therapies.

It is believed by many today, including the inventors, that stress is a root cause or foundation of many human ailments and debilitating conditions. It is a significant part of the present invention to prevent and treat stress by improved colored lighting techniques and equipment. The quantitative measurement of the effects of colored light therapies, as well as which color light treatments work best for a given individual, are important parts of the present invention. The exact dosage of colored light in the treatment of painful symptoms is critical and, therefore, must be quantified.

One of the major drawbacks of past colored light-therapy treatments has been the inability to quantitatively measure the effects that these therapies and regimens have upon the patients being treated. Treated individuals have experienced and felt a therapeutic difference during light therapy; many have been positively affected. However, to date it has not been possible to definitively and quantitatively determine the exact effects attributable to colored light treatments.

While it has been known for some time that individuals respond differently to colored light-therapy, the various treatments have, therefore, been conducted on an experimental, subjective, and sometimes hit-and-miss basis. This was particularly the case when such colored light therapies were combined with drug treatments, in order to relieve stress, as well as other, painful and related ailments. Different drugs were tried until the right drug and the right dosage fit a particular individual and situation, as the nervous system reacts differently to different dosages of colored light and drugs.

The present invention seeks to provide a means of measuring and recording both the physiological and psychological effects of colored light upon an individual. Such measurements quantify the effects that a particular treatment has upon the level of an individual's stress. Therefore, the inventive system provides the means by which specific colored light therapies can be scientifically and medically legitimized in the treatment and reduction of stress.

The current invention is a system that marries the colored light-testing machine, or, imagescope, of the aforementioned patent, with an apparatus that both physiologically monitors and records. This new apparatus will be referred to hereinafter as an "electrostressograph" (ESG). Individuals are treated with varying light colors, frequencies and patterns; the resultant physiological effects are then measured and recorded. In 1his fashion, what effect(s) the experimental colored light therapies and light treatments are having upon an individual can now be scientifically determined. With the aid of the electrostressograph, medications can now be tested to determine the efficacy of a particular type of drug upon a stress level being experienced by an individual.

A major component of the electrostressograph can comprise a glove to be worn by the patient during a particular colored light therapy or light treatment. The glove contains electrodes for measuring various bodily functions, such as temperature, skin conduction, blood pressure, etc. The patient may also be connected to an electromyelograph, an electroencephalograph, an electrocardiograph, an evoked-potential device, etc. A physiological monitoring system for analyzing the signals received from the electrodes can be a Johnson & Johnson (Model I-330) system, comprising modality modules that interface with, and which are controlled by, a computer.

An imagescope is used to bathe the patient with light of different colors, intensities and patterns. The same computer that controls the modality modules is also programmed so as to provide several different colored light-therapy sequences or treatments. A peripheral printer connected to the computer produces a printout, or, "electrostressogram," during the treatment. The computer is programmed to receive many different kinds of scientific, medical data. The computer processes this data in order to provide a diagnostic and therapeutic overview in both the diagnosis and the treatment of many physical and mental illnesses.

The imagescope may take the form of a multicolored television console, having a central mirror that can be attached to the surface thereof. The colored console can issue many different shades or patterns of color. The multicolored console can also comprise a cathode ray tube, around which an indwelling mirror is positioned. The imagescope can be designed as a colored, light-therapy stand, as is explained hereinafter.

A remote control can be manually used to change colors (i.e., white, red, orange, brown, green, yellow, blue, purple and gray, and other patterns of colors), as well as patterns thereof. The console's color intensity can be manually adjusted by the remote control. However, it may be more convenient to control the colored light sequence by the computer, since its software contains routines that automatically adjust colored light bathing, intensities and patterns. A strobing or flashing of color sequence is also contained in the routine.

Working the computer pad or keyboard, a doctor or technician sits behind the patient. The doctor or technician controls the remote control for changing the colors, and designates a color light-control sequence by typing the instructions into the computer keyboard.

The patient sits in a chair in front of the imagescope. Electrodes from the sensing system are attached to the patient, as aforementioned, who is enclosed in a curtained, light-free space, and is receiving only colored light that is emitted from the imagescope.

A remote-controlled camera or camcorder is perched atop the imagescope console and directed towards the patient's face, as the patient's facial expressions are photographed and recorded during "imageoscopy" testing. Data of pupillary reactions to the colors tested are also observed and recorded by the camera, as are changes in respiration. The sensing system can detect changes in blood pressure and store the data in computer memory, as well as provide a printout, or, electrostressogram.

The final printout, or electrostressogram, contains all of the sensed and recorded data, along with analyses thereof. Therapies are thus fashioned, using various forms of psychological therapies and/or drug treatments that are measured according to the color light sequences designated by the electrostressograph equipment. Certain tints of colors can be analyzed for their effects upon a patient's stress level. Drugs that have a calmative effect can be equated to different medications that neutralize specific amounts of stress in the patient. Correct color dosing can be established by measuring the quantitative decrease in stress that each color dosage has upon a patient. In this respect, the electrostressograph provides a means of properly dosing with colored light and/or drugs that was heretofore unavailable in the treatment of stress and related problems.

SUMMARY OF THE INVENTION

In accordance with the present invention, there is provided a color light-therapy apparatus for quantitatively measuring the effects that light has upon the relief of stress in an individual. The apparatus (referred to herein as an "electrostressograph") can also use color light treatments as a means of quantifying a type of medication and the appropriate dosage thereof that is required for both calming and treating a patient. The electrostressograph apparatus comprises the following five components: an "imagescope" console, including a video monitor, for bathing a patient in colored light and visually recording the effects that the colored light has upon the patient; a physiological monitoring system that monitors the patient and provides signals indicative of the patient's bodily functions, in response to various, light-bathing colors and colored-light sequences that are controlled with a programmable computer; a programmed computer with a peripheral printer, for receiving the signals from the physiological monitoring system and for processing the signals to provide a printout, or an "electrostressogram", of results of the stress analysis; and a keyboard, or remote control unit, for instructing the computer regarding the colored light or colored-light sequences being introduced to the patient via the imagescope console. The electrostressogram can then be faxed or sent via satellite to another medical facility. With the information being relayed to a control center, even an astronaut's stress level in space can be measured and treated.

It is an object of this invention to provide an apparatus which can quantify the effects that colored light therapies and light treatments have upon an individual.

It is an object of this invention to use electrostressography at the microscopic cellular level to test the stress-metabolism of normal cells and cancer cells (pathological) for medical research.

It is another object of this invention to provide a means by which drug therapies can be related to colored light effects, so that the two therapies can be combined into a synergistic treatment of stress.

It is a further object of this invention to provide a means to screen, diagnose, treat, and prevent medical illnesses caused by stress.

It is a still further object of this invention to provide a research means to study the vibratory, electromagnetic (auras) and spiritual systems of the body by the use of colored light.

It is still another object of the invention to provide a research means to study the immunology system, the creativity system and the spiritual system of the human body.

These and other objects of this invention will become more apparent and better understood, when considered in conjunction with the subsequent FIGURES and detailed description.

BRIEF DESCRIPTION OF THE DRAWINGS

A complete understanding of the present invention may be obtained by reference to the accompanying drawings, and subsequent, detailed description thereof, in which.

DESCRIPTION OF THE PREFERRED EMBODIMENT

Generally speaking, the invention features an apparatus for quantifying the effects that colored light therapies and light treatments and diagnostic screenings have upon an individual. The apparatus features an "imagescope" console that bathes a patient in differing colored light sequences. A physiological monitoring unit monitors the bodily functions of the individual, as the various light treatments are applied. A computer analyzes the monitored data, and produces a printout, or an "electrostressogram", which details the quantitative effects of the colored light therapies.

Figure 1:
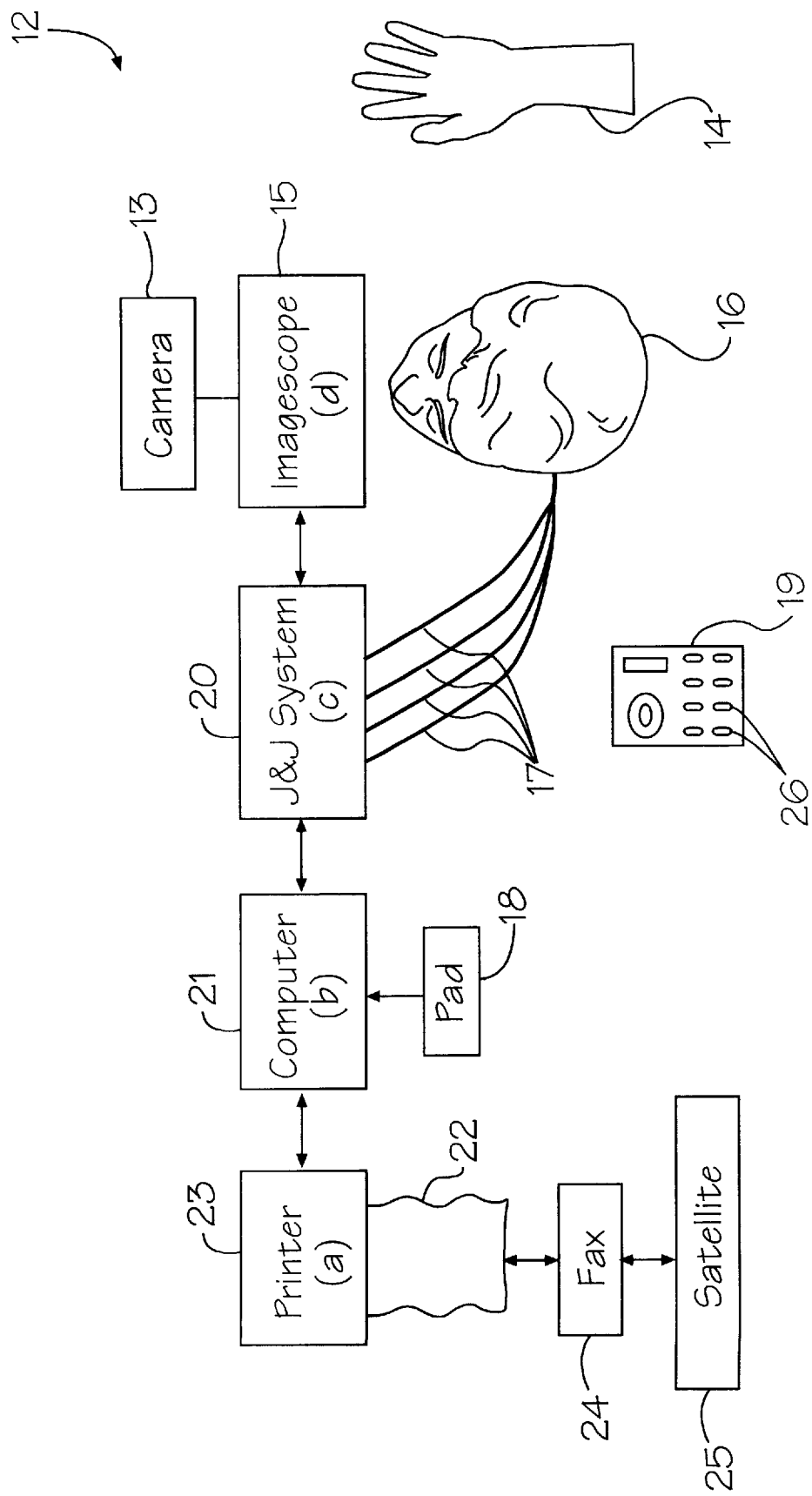
FIG. 1 illustrates a schematic, block diagram of the apparatus of this invention.

Now referring to FIG. 1, a block diagram illustrates a schematic of the light-therapy apparatus 12 of this invention, hereinafter referred to as an "electrostressograph system." A major component of the electrostressograph system 12 comprises a glove 14 that is to be worn by the patient 16 during colored light therapy or light treatment. The glove 14 contains electrodes (not shown) for measuring various bodily functions, such as temperature, skin conduction (EMG), blood pressure, etc. The glove 14 is connected to a physiological monitoring system 20 for analyzing the signals received from the electrodes in the glove 14. Other electrodes 17 are connected between the patient 16 and the physiological monitoring system 20, which can comprise modality modules (not shown) such as an electromyelograph, an electroencephalograph, an electrocardiograph, an evoked-potential device, etc. The physiological monitoring system can be a Johnson & Johnson Model I-330 system, having modality modules that interface with, and which are controlled by, the computer 21.

An imagescope console 15 is used to bathe the patient 16 with light of different colors, intensities and patterns. The computer 21 controlling the modality modules is also programmed to provide several different light-therapy sequences or treatments, to be introduced through the imagescope console 15. A peripheral printer 23 connected to the computer 21 produces a printout or an "electrostressogram" 22 during the treatment. The computer 21 is programmed to receive various kinds of scientific and medical data. The computer 21 processes the scientific and medical data to provide a diagnostic overview that is used in the treatment of stress. The data can be relayed to other medical centers or facilities, and can also be beamed via satellite to and from space, so as to treat space travelers and astronauts.

The imagescope console 15 may take the form of a multicolored television console, having a central mirror that can be attached to the surface of the console (not shown). This colored console can issue many different shades of color, color sequences, color patterns, amplified and lasered light, etc. The multicolored console can also comprise a cathode-ray tube, around which an indwelling mirror is positioned. A more detailed description of the components of the imagescope console 15 can be obtained hereinafter, with reference to FIG. 2, that make up the light therapy stand. Another imagescope form may be the use of colored laser light that can be reflected off of a mirrored surface for imageoscopic diagnosis and treatment.

A remote control 19 can be manually used to change colors (white, red, orange, brown, green, yellow, blue, purple and gray), as well as color sequences, patterns, hues, tints, etc. The color intensity provided by the imagescope console 15 can be manually adjusted by the remote control 19. However, it may be more convenient to control the light sequence by the computer 21, since its software contains routines that automatically adjust colored light bathing, intensities and patterns. A strobing or flashing of color sequence is also contained in the routine.

A doctor or technician (not shown) sits behind the patient 16 working the computer pad or keyboard 18 or the remote control 19. The doctor or technician changes the colors and designates particular colored light-control sequences by typing the instructions into the computer keyboard 18, or depressing numerical buttons 26 on the remote control 19.

The patient 16 sits in a chair in front of the imagescope console 15, as shown. Electrodes 17 of the sensing system are attached to the patient 16, as aforementioned. The patient 16 is enclosed in a curtained, light-free space, and receives only colored light that is emitted from the imagescope console 15.

A remote-controlled camera, camcorder or video camera 13 is perched atop the imagescope console 15, and is directed towards the face of the patient 16. The camera 13 records the facial expressions, as well as inhalation and exhalation patterns during the "imageoscopy" testing. Data of pupillary reactions to the colors tested are also recorded by the camera 13. The camera 13 can be hooked to the computer 21, and the recorded images can be stored in a CD ROM unit (not shown) contained in the computer 21 or in the computer memory.

The final printout or electrostressogram 22 contains all of the sensed and recorded data, along with analyses thereof. Colored Light therapies are thus fashioned, using various forms of psychological therapies and/or drug treatments that are measured according to the colored light sequences designated by the electrostressogram equipment. Certain tints of colors can be analyzed for their therapeutic effects upon the stress level of a patient 16. Drugs that have a calmative effect can be measured and equated with different therapeutic dosages of color that neutralize specific amounts of stress (such as anxiety, depression and anger) in a patient. Correct dosing can be established by measuring the quantitative decrease in stress that each colored light dosage has upon a patient. In this respect, the electrostressograph system 12 provides a means of light dosing (along with combinations of Light treatment and drug medication) that was heretofore unavailable in the treatment of stress and related problems. For example, the electrostressograph can be used to prevent and/or treat tardive dyskinesia; it may be the first such instrument to do so. Electrostressography will scientifically prove the therapeutic effects of psychotherapy.

Imageoscopic analysis provides for two colored light therapies: colored refraction therapy and colored self-image analysis therapy. Electrostressography monitors a patient's responses to particular colors, in order to determine the most comfortable color for that individual. This color can then be tinted on a pair of eyeglasses, for example, thus helping to mute past coded stressful experiences and the daily stress being experienced by the individual. This procedure is described in the aforementioned U.S. Pat. No. 5,064,410.

Once the most calmative color is determined for a patient, electrostressography can then be used in self-image analysis to treat the causes of stress. After electrostressography has determined the stressful colors for the patient, each stressful color is desensitized with the imagescope until all of the stressful colors are neutralized and the patient is generally free of past, encoded, color-induced stress. An electrostressogram is taken before therapy; after the desensitization of each color; and at the end of therapy, when all stressful colors have been desensitized.

Figure 2:
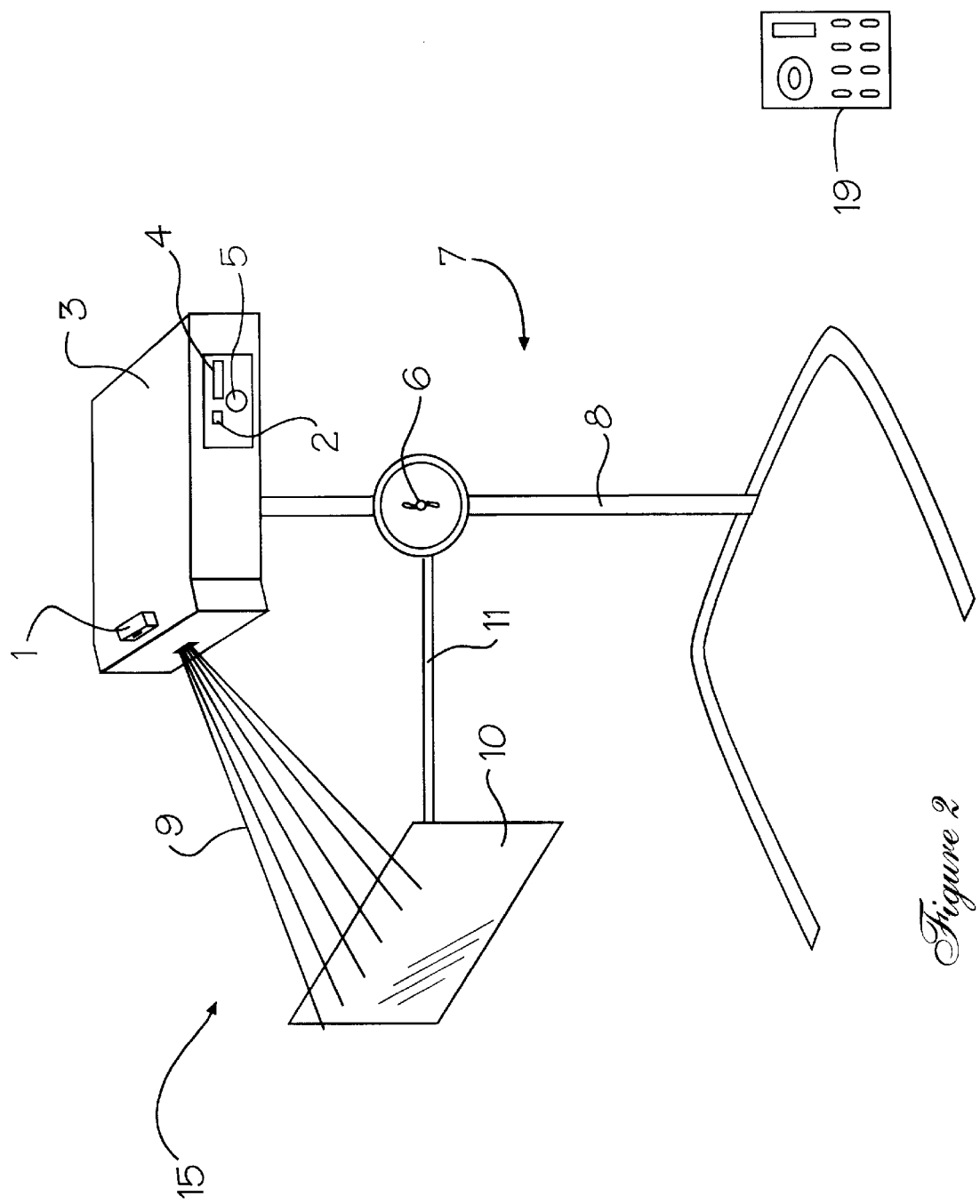
FIG. 2 depicts a schematic view of the imagescope console shown in the block diagram of FIG. 1.

Referring to FIG. 2, a typical imagescope console 15 is shown in more detail. A remote-controlled light-therapy stand 7 is used to self-diagnose a patient's past, color-related stress acquired over his or her lifetime. This color information is then used to desensitize the induced, color stresses. A patient 16 can counter the stress with the use of color-tinted eyeglasses, in order to reduce a particular reaction to newly experienced stresses, thus controlling or preventing such stress from reaching undesirable levels of discomfort. The light-therapy stand 7 can be made with a telescopic, vertical bar 8 that can permit the lowering or increasing of the stand's height. The adjustable mirror winged screw 6 permits the height adjustment of the mirror. The mirror arm 11 inserts into a swivel ball & socket joint affixed to the back of the mirror 10 permitting the mirror 10 to be angulated at a desired position for the patient 16 to view his/her image.

The imagescope console 15 can comprise a light projector 3 that projects light 9, after power switch 2 is activated, toward the face and over the head of a patient, above a mirror, bathing the patient's face in a specific colored image reflected in mirror 10 while the patient is sitting in front of the imagescope console 15. The light projector 3 can comprise an adjustable rheostat 4 for manually changing the color intensity of the light, but the color is usually controlled with a computer 21 (FIG. 1). Likewise, the light projector 3 can comprise a switch 5 for providing strobing or flashing light effects for light 9. A camera or camcorder 1 can be mounted on top of the light box 3, so as to record the effects of the light testing. Both the patient 16 and the imagescope console 15 are disposed in a curtained-off, or darkened, enclosed area of space, in which the patient is free of any environmental or background light.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A colored light-therapy apparatus for quantitatively measuring the effects that colored light has upon the relief of stress in an individual, comprising:

colored light-bathing means including a mirror for applying colored light onto an individual, through colored light treatments or colored light therapy to said individual;

sensing means disposed adjacent said individual for sensing the effects that said colored light treatments or colored light therapy have upon said individual, and for generating signals indicative of physiological changes in response to said colored light treatments or colored light therapy;

physiological monitoring means connected to said sensing means for receiving said generated signals from said sensing means, said physiological monitoring means monitoring the physiological changes in said individual in response to said colored light treatments or colored light therapy, and generating data with respect to said physiological changes; and a programmable computer, connected to said physiological monitoring means and said colored light-bathing means, for analyzing the generated data from the physiological monitoring means and for providing a physiological analysis of the individual in response to said colored light treatments or colored light therapy, as well as for controlling said colored light being applied to said individual.

2. The colored light-therapy apparatus in accordance with claim 1, further comprising facial expression-change recording means disposed adjacent said individual, for recording changes in facial expression of said individual, in response to said colored light treatments or colored light therapy.

3. The colored light-therapy apparatus in accordance with claim 1, further comprising pupillary-change recording means disposed adjacent said individual for recording changes in pupils of said individual, in response to said colored light treatments or colored light therapy.

4. The colored light-therapy apparatus in accordance with claim 1, further comprising a printer connected to said computer for providing a record of said physiological analysis.

5. The colored light-therapy apparatus in accordance with claim 1, further comprising an input means disposed adjacent to, and operatively connected to, said colored light-bathing means for changing characteristics of said light being applied onto said individual.

6. The colored light-therapy apparatus in accordance with claim 1, wherein said computer is operatively connected to said colored light-bathing means for controlling colored light-bathing sequences applied onto said individual.

7. The colored light-therapy apparatus in accordance with claim 1, wherein said sensing means comprises a glove containing electrodes, for attachment to said individual.

8. A colored light-therapy apparatus for quantitatively measuring the effects that colored light has upon the relief of stress in an individual, comprising:

colored light-bathing means including a mirror for applying colored light onto an individual, through colored light treatments or colored light therapy to said individual;

sensing means disposed adjacent said individual for sensing the effects that said colored light treatments or colored light therapy have upon said individual, and for generating signals indicative of physiological changes in response to said colored light treatments or colored light therapy;

physiological monitoring means connected to said sensing means for receiving said generated signals from said sensing means, said physiological monitoring means monitoring the physiological changes in said individual in response to said colored light treatments or colored light therapy, and generating data with respect to said physiological changes; and a programmable computer, connected to said physiological monitoring means, for analyzing the generated data from the physiological monitoring means, and for providing a physiological analysis of the individual, in response to said colored light treatments or colored light therapy.

9. The colored light-therapy apparatus in accordance with claim 8, further comprising facial expression-change recording means disposed adjacent said individual for recording changes in facial expression of said individual, in response to said colored light treatments or colored light therapy.

10. The colored light-therapy apparatus in accordance with claim 8, further comprising pupillary-change recording means disposed adjacent said individual for recording changes in pupils of said individual, in response to said colored light treatments or colored light therapy.

11. The colored light-therapy apparatus in accordance with claim 8, further comprising a printer connected to said computer for providing a printout of said physiological analysis.

12. The colored light-therapy apparatus in accordance with claim 8, further comprising an input means disposed adjacent to, and operatively connected to, said colored light-bathing means for changing characteristics of said colored light being applied onto said individual.

13. The colored light-therapy apparatus in accordance with claim 8, wherein said computer is operatively connected to said colored light-bathing means for controlling said colored light-bathing of said individual.

14. A colored light-therapy apparatus for quantitatively measuring the effects that colored light has upon the relief of stress in an individual, comprising:

colored light-bathing means including a mirror for applying light onto an individual, through colored light treatments or colored light therapy to said individual;

sensing means disposed adjacent said individual for sensing the effects that said colored light treatments or colored light therapy have upon said individual, and for generating signals indicative of physiological changes in response to said colored light treatments or colored light therapy;

physiological monitoring means connected to said sensing means for receiving said generated signals from said sensing means, said physiological monitoring means monitoring the physiological changes in said individual in response to said colored light treatments or colored light therapy, and generating data with respect to said physiological changes;

a programmable computer, connected to said physiological monitoring means, for analyzing the generated data from the physiological monitoring means, and for providing a physiological analysis of the individual, in response to said colored light treatments or colored light therapy; and recording means connected to said programmable computer for providing a record of said physiological changes in said individual, in response to said colored light treatments or colored light therapy.

15. The colored light-therapy apparatus in accordance with claim 14, further comprising facial expression-change recording means disposed adjacent said individual for recording visual changes in facial expression of said individual, in response to said colored light treatments or colored light therapy.

16. The colored light-therapy apparatus in accordance with claim 14, further comprising pupillary-change recording means disposed adjacent said individual for recording changes in pupils of said individual, in response to said colored light treatments or colored light therapy.

17. The colored light-therapy apparatus in accordance with claim 14, wherein said recording means includes a printer connected to said computer, for providing a printed record of said physiological analysis.

18. The colored light-therapy apparatus in accordance with claim 14, further comprising an input means disposed adjacent to, and operatively connected to, said colored light-bathing means for changing characteristics of said colored light being applied onto said individual.

19. The colored light-therapy apparatus in accordance with claim 14, wherein said computer is operatively connected to said colored light-bathing means for controlling said colored light-bathing of said individual.

20. The colored light-therapy apparatus in accordance with claim 14, wherein said sensing means comprises a glove containing electrodes, for attachment to said individual.

* * * * *